(12) United States Patent
Hurvitz et al.

(10) Patent No.: US 7,499,169 B2
(45) Date of Patent: Mar. 3, 2009

(54) FUEL CELL AND PRODUCT OF COMBUSTION HUMIDITY SENSOR

(75) Inventors: Nathan N. Hurvitz, Sherman Oaks, CA (US); Carl Allan Kukkonen, Dana Point, CA (US)

(73) Assignee: VIASPACE Inc., Pasadena, CA (US)

( * ) Notice: Subject to any disclaimer, the term of this patent is extended or adjusted under 35 U.S.C. 154(b) by 60 days.

(21) Appl. No.: 11/780,412

(22) Filed: Jul. 19, 2007

(65) Prior Publication Data

US 2008/0088821 A1 Apr. 17, 2008

Related U.S. Application Data

(60) Provisional application No. 60/832,244, filed on Jul. 19, 2006.

(51) Int. Cl.
*G01N 21/00* (2006.01)

(52) U.S. Cl. .................. 356/432; 356/436; 356/437
(58) Field of Classification Search .................. None
See application file for complete search history.

(56) References Cited

U.S. PATENT DOCUMENTS

| 4,491,730 | A | * | 1/1985 | Pedersen | 250/343 |
| 4,578,762 | A | * | 3/1986 | Wong | 702/32 |
| 4,943,161 | A | * | 7/1990 | Michaelis et al. | 356/437 |
| 2005/0036147 | A1 | * | 2/2005 | Sterling et al. | 356/436 |
| 2007/0229834 | A1 | * | 10/2007 | Patel et al. | 356/432 |

* cited by examiner

*Primary Examiner*—Michael P Stafira

(57) ABSTRACT

Densities of water vapor can be detected and quantified at a high sampling rate for a gas. The gas can be contained within a sample chamber within or outside of an instrument enclosure. A first split beam passes through the enclosure and the sample chamber while a second split beam that passes only through the enclosure provides a reference that can be used to correct for ambient humidity in the instrument enclosure.

35 Claims, 5 Drawing Sheets

FUEL CELL AND PRODUCT OF COMBUSTION HUMIDITY SENSOR

RELATED APPLICATIONS

The present patent application claims priority under 35U.S.C. §119 to U.S. Provisionl Patent Application Ser. No. 60/832,244, filed on Jul. 19, 2006, and entitled "Fuel Cell Test Station Humidity Sensor", the disclosure of which is incorporated by reference herein in its entirety.

TECHNICAL FIELD

The subject matter disclosed herein relates to detection and measurements of water vapor densities in gas streams, including but not limited to gas streams for fuel cells and exhaust streams from combustion processes.

BACKGROUND

The performance of fuel cells using a polymer electrolyte membrane (PEM) or other comparable means of controlling the flow of ions in an electrolytic reaction can be quite sensitive to the moisture level of the membrane. Proper hydration of the membrane can be necessary for the membrane to conduct protons and thereby create the movement of charged particles that creates an electric current. Moisture can be provided by water vapor in the incoming air or fuel stream (for example hydrogen) to maintain the membrane at an appropriate and desirable level of hydration. Accurate, reliable, robust, real time measurement of water vapor concentrations is necessary to assure reliable and efficient operation of the fuel cell.

SUMMARY

In one aspect an apparatus includes an instrument enclosure and a light source that emits a light beam directed within the instrument enclosure. A beam splitter is disposed within the instrument enclosure to split the light beam into a first split beam and a second split beam. A sample chamber configured to accept a flowing humidified gas stream can optionally be positioned within or outside of the instrument enclosure and disposed so that the first split beam passes through the sample chamber over a sample chamber path length. A first detector is positioned within the instrument enclosure and disposed in the path of the first split beam after the first split beam passes through the sample chamber. The first detector quantifies a first intensity of light transmitted in the first split beam as the first split beam traverses a first instrument enclosure path length within the instrument enclosure and the sample chamber path length. A second detector is positioned within the instrument enclosure and disposed in the path of the second split beam. The second detector quantifies a second intensity of light transmitted in the second split beam as the second split beam traverses a second instrument enclosure path length within the instrument enclosure. The second instrument enclosure path length being approximately equal to the first instrument path length. A controller is configured to receive and interpret a first signal from the first detector and a second signal from the second detector to calculate the water vapor partial pressure in the flowing humidified gas stream.

The apparatus can optionally also include an inlet to the sample chamber and an outlet from the sample chamber, and a fuel cell system connected to the inlet. The fuel cell system can provide the flowing humidified gas stream. In this variation, a connector configured to connect a fuel cell to the outlet can be provided such that the flowing humidified gas stream from the fuel cell system is supplied to the fuel cell. In another variation, a connector configured to connect a fuel cell to the inlet can be provided such that the flowing humidified gas stream from the fuel cell is supplied back to the fuel cell system. In another variation, a connector configured to connect a fuel cell to the inlet can be provided such that the flowing humidified gas stream from the fuel cell is vented to atmosphere. In another optional variation, the flowing humidified gas stream can be an exhaust stream emitted from a combustion device connected to an inlet on the sample chamber. The combustion device can optionally be an internal combustion engine. The apparatus can optionally further include an automobile with an internal combustion engine that comprises an exhaust connected to an inlet on the sample chamber. The exhaust can provide the flowing humidified gas stream and the controller can optionally provide a feedback signal regarding the partial pressure or density of water vapor in the exhaust.

In an interrelated aspect, a method includes splitting a beam of light from a light source into a first split beam and a second split beam within an instrument enclosure and flowing a humidified gas stream through a sample chamber. In optional variations, the sample chamber can optionally be positioned inside or outside of the instrument enclosure or the sample chamber can optionally be positioned outside of the instrument enclosure and include a portion of a system being analyzed. The first split beam is directed through the sample chamber and to a first detector positioned within the instrument enclosure so that the first detector can quantify a first intensity of light transmitted in the first split beam as the first split beam traverses a first instrument enclosure path length within the instrument enclosure and a first sample chamber path length within the sample chamber. The second split beam is directed to a second detector positioned within the instrument enclosure so that the second detector can quantify a second intensity of light transmitted in the second split beam as the second split beam traverses a second instrument enclosure path length within the instrument enclosure. The second instrument enclosure path length is approximately equal to the first instrument path length. A density (or partial pressure) of water vapor in the sample chamber is calculated and promoted based on the first intensity of light and the second intensity of light. The density can optionally be promoted by displaying, transmitting, or storing the density of water vapor in the sample chamber.

In optional variations, the light source can be selected from a group consisting of a vertical cavity surface emitting laser, a horizontal cavity surface emitting laser, a quantum cascade laser, a distributed feedback laser, a color center laser, a light emitting diode, and an incandescent lamp. The light source can be a tunable diode laser controlled by the controller. In this variation, the light beam can include a range of wavelengths and the controller can tune the tunable diode laser across the range of wavelengths, demodulate the first signal and second signal to determine a first absorption spectrum for the first split beam and a second absorption spectrum for the second split beam, and calculate the water vapor density in the flowing gas stream based on the first absorption spectrum and the second absorption spectrum. The light source can optionally emit light with a wavelength in a range of about 1.35 to 1.39 µm or optionally at a wavelength of approximately 1.12 µm, 1.37 µm, 1.88 µm, 2.35 µm, 2.70 µm, 3.00 µm, 6.00 µm, or 6.50 µm. The sample chamber can be maintained at a temperature above approximately 105° C., and/or the instrument enclosure can be maintained at a temperature in a range of approximately 20° to 35° C. The light source can be maintained at a temperature in a range of approximately 20° to 40° C. In another variation, the sample chamber can be maintained at a temperature that can be adjustable.

DESCRIPTION OF THE DRAWINGS

This disclosure may be better understood upon reading the detailed description and by reference to the attached drawings, in which.

DETAILED DESCRIPTION

Figure 1:
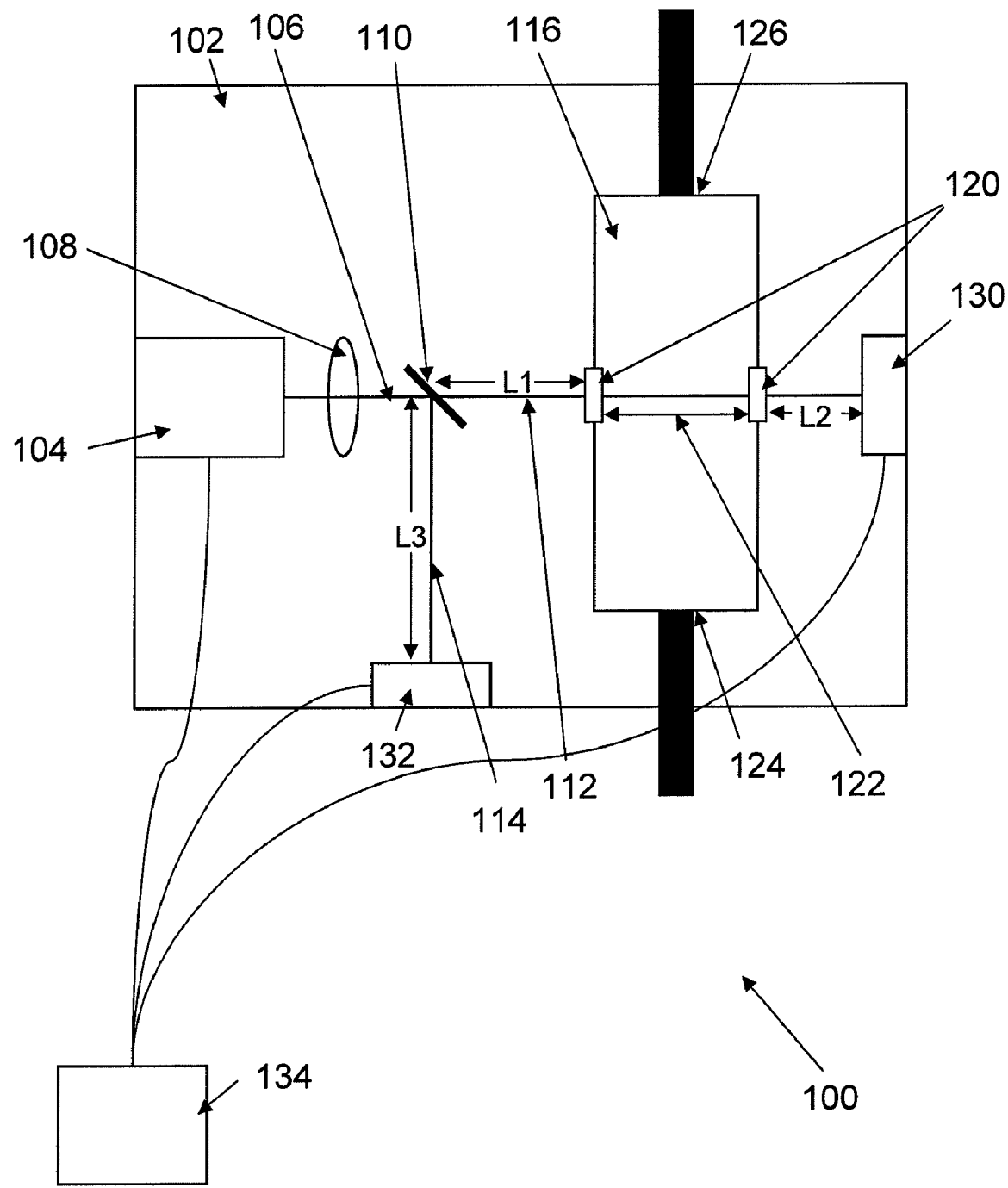
FIG. 1 is a block diagram showing an example of a humidity sensor.

A humidity sensor as well as methods of using the same are provided. The subject matter disclosed is capable of making measurements of the humidity or changes in the humidity of a flowing gas stream quickly, for example on a sample cycle of approximately one second. The sample chamber in which the optical measurements are made can be heated sufficiently to evaporate liquid water that is entrained in the gas stream. In the event that entrained water droplets in the gas stream are not evaporated, they will still not affect the humidity reading of the humidity sensor, as liquid water absorbs light at different wavelengths than gaseous water vapor. In case of flooding of the humidity sensor sample chamber with liquid water, recovery can be automatic and rapid due to the heating of the sample chamber as described in greater detail below.

Various aspects of the subject matter disclosed herein can provide one or more advantages, including but not limited to accurate, quick, and reproducible measurements of water vapor partial pressure. The quick time response of systems, methods, techniques, articles of manufacture, and the like employing the current subject matter can make them well suited for use in measurement and control loops for monitoring and adjusting the water vapor densities in flowing gas streams, such as for example gas streams used in fuel cell operation or combustion process monitoring and/or control. Water vapor partial pressure can be measured for flowing gas streams at relatively high humidity at high temperatures with an in situ sensor.

Sensors as described herein can be used as part of a fuel cell system in normal operation. In such an application, the gas stream being analyzed can be a fuel stream that can optionally contain hydrogen, methane, natural gas, or other fuel gases. In such an application, the gas stream being analyzed can otherwise be an oxidizer stream that can optionally contain air, an oxygen/nitrogen mix, or other oxidizer gas combinations. A sensor as described here can also be used as part of a fuel cell system for development of, for testing of, or for providing maintenance to a fuel cell or fuel cell system. A sensor such as described here can also optionally be used downstream of a combustion system or device, such as for example an internal combustion engine in an automotive application, to measure the partial pressures of products of combustion (POC). The currently disclosed subject matter also has potential applications in the metal processing industry, such as for example in a furnace or heat treating application and also in other high humidity, high temperature environments such as for example a sauna.

Such sensors can in one variation be installed in series between a fuel cell humidifier and a fuel cell and/or fuel cell stack being analyzed such that the humidity level of a gas stream is measured prior to its admission to the fuel cell. The humidity measurement can be used to optimize performance of the fuel cell, which may depend critically on the humidification state of the fuel cell membrane (among other factors). Such sensors can also be installed after the fuel cell on either of the two exhaust gas streams to measure the humidity level of the exhaust gas. The device, systems and techniques described here can be used with any fuel cell, fuel cell stack, fuel cell testing instrumentation, or fuel cell system utilizing any gaseous anode or cathode gas streams (fuel or oxidizer gas streams) that may be humidified with water vapor, including, but not limited to, hydrogen, air, oxygen, and nitrogen.

The subject matter disclosed herein can also be used to measure partial pressure of water vapor and/or other components of an exhaust gas stream from a combustion process, such as for example, from an internal combustion engine in perhaps an automotive application. The products of combustion (POC) in the exhaust gas stream of an internal combustion engine of an automobile may be of interest to scientists and engineers researching and developing engine design, fuel/air ratio, studying fuel formulations and their POCs. This may be particularly useful in characterizing the cold start-up exhaust products of the engine, where stoichiometric calculations may not be employed. Characterization of POCs may also be of interest to persons or organizations involved with environmental air quality. In another variation, the subject matter disclosed herein can be used to measure the water vapor partial pressure in the metal processing industry, such as for example in a furnace or heat treating application. In another variation, the subject matter disclosed herein can be used to measure the water vapor partial pressure within a sauna or other application which has high humidity and high temperatures. In another implementation, a humidity sensor can be used to provide control of a humidification system or alternatively of a combustion system, one variation being an internal combustion engine for an automotive application.

FIG. 1 is a block diagram 100 showing an example of a humidity sensor. As shown in FIG. 1, an instrument enclosure 102 is provided that encloses most of the components of the sensor. The interior volume of the instrument enclosure 102 can optionally be temperature controlled, such as for example at a temperature near room temperature, such as for example in a range of approximately 20 to 35° Celsius. Various mechanisms such as for example a thermostat with a feedback control to a heating element or the like, can be used to maintain the instrument enclosure 102 and the components therein at a preset and fixed temperature.

A light source 104, such as for example a laser, that produces a continuous or pulsed beam 106 can be positioned within the instrument enclosure 102 such that it is maintained at the preset temperature of the instrument enclosure 102. In some implementations, the light source 104 can be positioned outside of the instrument enclosure 102, especially if fiber coupled. In other implementations, the light source 104 itself can be temperature controlled, such as for example at a temperature in a range of approximately 20° to 40° Celsius. Various mechanisms or techniques such as for example a thermostat with a feedback control to a heating and/or cooling element or the like, can be used to maintain the light source 104 at a preset and fixed temperature. The light source can be chosen to emit a wavelength or range of wavelengths that coincide with a spectral feature of the gas to be measured. In the example of a humidity sensor, the chosen wavelength or wavelength range can coincide with a wavelength at which a spectral absorption feature of gas-phase water molecules is distinguishable from other components in the gas stream or sample. In one example, the light source can provide light in the wavelength range of 1.35 to 1.39 microns (μm). The absorption spectra of water vapor are well known. Strong absorption peaks occur in bands that include, but are not limited to, bands around wavelengths of 1.12 μm, 1.37 μm, 1.88 μm, 2.35 μm, 2.70 μm, 3.00 μm, 6.00 μm, and 6.50 μm. Methods, techniques, apparatuses, and systems as described herein can also be used to measure other gas-phase species in gas samples or flowing gas streams. For analysis of other analytes, an appropriate wavelength or wavelength range can be chosen.

The beam 106 from the light source 104 can optionally be focused or directed by one or more collimating lenses 108 or other optical components. The light source 104 can optionally be a tunable diode laser such as for example a distributed feedback laser (DFB), a vertical cavity surface emitting laser (VCSEL), a horizontal cavity surface emitting laser (HC-SEL), or the like. These lasers can be direct emitters or fiber coupled. Quantum cascade lasers can also be utilized as can other lasers capable of producing a beam of incident light in the desired wavelength range. An LED ("light-emitting diode") or alternatively an incandescent light can also optionally be used as the light source 104. In implementations with an LED or an incandescent light as the light source 104, a band pass filter can optionally be installed after the light source to permit only selected wavelengths of light to pass.

The beam 106 is split by a beam splitter 110 into a first split beam 112 and a second split beam 114. The beam splitter 110 can optionally have a polka dot reflective pattern in the path of the light beam 106. In other implementations, the beam splitter 110 can optionally be partially reflecting, such as for example a partially silvered beam splitter in the path of the light beam 106. In other implementations, a mirror can partially occlude the light beam 106 and reflect a portion of the laser beam to the second detector 132.

The first split beam 112 passes through a sample chamber 116, either directly or optionally using one or more optical components including but not limited to fiber optics, mirrors, and the like. The sample chamber 116 can include one or more windows 120 that are transparent to the wavelength or wavelength range produced by the light source 104. The sample chamber can be maintained at an elevated temperature relative to the instrument enclosure 102 to prevent condensation of water from the humidified gas stream. In one example, the sample chamber 116 can be insulated and can include a mechanism that heats and maintains the sample chamber 116 at a temperature of 105° C. or greater. In another example, the sample chamber 116 can be insulated and can include a mechanism that heats and maintains the sample chamber 116 at a temperature that can be adjusted through a range of temperatures via a control mechanism operated by the humidity sensor user. In still another example, the sample chamber 116 can be insulated and can include a mechanism that heats and maintains the sample chamber 116 at a temperature that may be adjusted through a range of temperatures via an automated control mechanism. The first split beam 112 can pass through the window or windows 120, through a gas contained within the sample chamber 116, and then out through either the same window 120 through which it entered, or alternatively, through a second window 120. If the sample chamber 116 includes only one window 120, a mirror can be provided to reflect the first split beam 112 back out of the one window 120. More than one mirror can also be used to extend the distance the first split beam 112 travels within the sample chamber 116. Regardless of the configuration, the first split beam 112 traverses a sample chamber path length 122 within the sample chamber 116. The sample chamber 116 can have an inlet 124 and an outlet 126 through which gas can flow into and out of, respectively, the sample chamber 116. In some implementations, the sample chamber 116 can optionally be located outside of the instrument enclosure 102, such as could be formed by existing piping or a chamber in the system being measured, for example in an in-situ measurement. The instrument enclosure 102 can be maintained at or near normal room temperatures as noted above and can be sufficiently insulated from the sample chamber 116 such that it is possible to maintain thermal control of the light source and/or the detectors and other components within the instrument enclosure 102 at one temperature and the sample chamber 116 at an elevated temperature that may differ from the instrument enclosure temperature by, for example as much as about 70 to 85° C. or more. The gas stream flowing through the sample chamber 116 can optionally be at ambient pressure, for example approximately 1 atmosphere, or alternatively at a vacuum or under positive pressure.

After passing through the sample chamber 116, the first split beam 112 impinges, either directly or optionally using one or more optical components including but not limited to fiber optics, mirrors, and the like, a first detector 130 that quantifies the intensity of light at the wavelength or wavelength range of the light source 104. In addition to the sample chamber path length 122 that the first split beam 112 traverses on its way from the beam splitter 110 to the first detector 130, the first split beam 112 also traverses a first instrument enclosure path length during which it passes through the air or other gas mixture that is present in the instrument enclosure 102. This air or other gas mixture can contain a significant density of water vapor that can bias the inferred water vapor density in the sample chamber 116. In the example shown in FIG. 1, the first instrument enclosure path length is the sum of the distance L1 between the beam splitter and the sample chamber window 120 through which the first split beam 112 enters the sample chamber 116 and the distance L2 between the sample chamber window 120 through which the first split beam 112 exits the sample chamber 116 and the first detector 130.

After the beam splitter 110, the second split beam 114 impinges a second detector 132, either directly as shown in FIG. 1 or optionally via one or more optical components including but not limited to fiber optics, mirrors, and the like. The second split beam 114 traverses a second instrument enclosure path length during which it passes through the air or other gas mixture that is present in the instrument enclosure 102. In the example of FIG. 1, this second instrument enclosure path length is the distance L3 between the beam splitter 110 and the second detector 132. The components in the instrument enclosure 102 can be configured such that the second instrument enclosure path length is at least approximately equal to the first enclosure path length. In the example of FIG. 1, this relationship can be expressed as L1+L2=L3.

The first detector 130 and the second detector 132 can each be a photo detector. One photo detector is an indium gallium arsenide (InGaAs) photodiode sensitive to light in the 1200 to 2600 nm wavelength region. For longer wavelengths, an indium arsenide photodiode, sensitive for wavelengths up to approximately 3.6 μm, can be used. Alternatively, indium antimonide detectors are currently available for wavelengths as long as approximately 5.5 μm. Both of the indium devices operate in a photovoltaic mode and do not require a bias current for operation. These photodetectors, which lack low frequency noise, are advantageous for DC or low frequency applications. Such detectors are also advantageous for high speed pulse laser detection, making them particularly useful in trace gas absorption spectroscopy. Other photodetectors, such as for example indium arsenide (InAs), silicon (Si), or germanium (Ge) photodiodes and mercury-cadmium-telluride (MCT) and lead-sulfide (PbS) detectors, can also be selected and used to match the wavelength of the light source 104.

A controller or control unit 134 can be included to receive signals output from the first detector 130 and the second detector 132 and to process these signals to calculate a partial pressure of water vapor in the sample chamber 116. Absorption of light from the first split beam 112 due to water vapor in the instrument enclosure 102 along the first enclosure path length (L1+L2 in FIG. 1) can be corrected by using the measured absorption of the second split beam 114 along the second instrument enclosure path length (L3) by assuming that the water vapor density in the instrument enclosure 102 is uniform through the instrument enclosure 102. The controller or control unit 134 can include one or more processors coupled to a memory that stores instructions in computer readable code. When executed on the processor or processors, the instructions can implement a method, such as for example that described above, to analyze the humidity in a flowing gas stream or fixed gas sample volume. If the control unit 134 is electronically connected to the light source 104, it can optionally control the light source 104. For example, if the light source 104 is a tunable diode laser, the control unit 134 can control the scan rate and also interpret the direct voltage measurements by the first detector 130 and the second detector 132. The control unit 134 can also adjust the modulation amplitude as necessary to improve spectral resolution. The tunable laser wavelength can be varied by changing the injection current while keeping the laser temperature constant. The temperature of the laser can be controlled, and thereby tuned to an appropriate water vapor absorption peak wavelength, independently from the temperature of the sample chamber 116 or of the temperature of the instrument enclosure 102. In some implementations, the tunable laser, as the light source 104, can optionally be temperature controlled, such as for example at a temperature in a range of approximately 20° to 40° C. Various mechanisms and techniques such as for example a thermostat with a feedback control to a heating and/or cooling element or the like in thermal contact with the tunable laser, can optionally be used to maintain the tunable laser at a preset and fixed temperature. In some implementations, the control unit 134 can provide process control functions to regulate the instrument enclosure 102 temperature.

A sensor as described herein can utilize a laser whose spectral bandwidth is much narrower than the bandwidth of the absorption lines of interest. Such an arrangement allows for single line absorption spectroscopy in which it is not necessary to scan the entire width of the absorption line or even the peak absorption feature of the line. The wavelength of the laser can be chosen to be one at which there is a resolvable difference in the relative absorbance of water molecules and the other components of the gas to be measured. Direct absorption spectroscopy is insensitive to background gas composition. By measuring direct absorption, noise due to variations in the background gases can be eliminated or substantially reduced. In some implementations, the humidity sensor uses direct absorption spectroscopy. This approach can potentially be beneficial in cases such as measurement of water vapor in the products of combustion wherein the composition of the gases in the gas stream can vary.

In some implementations, an absorption spectrometer system can employ a harmonic spectroscopy technique in connection with a TDL light source. Harmonic spectroscopy as used in the disclosed subject matter involves the modulation of the TDL laser (DFB or VCSEL) wavelength at a high frequency (kHz-MHz) and the detection of the signal at a multiple of the modulation frequency. If the detection is performed at twice the modulation frequency, the term second harmonic or "2f" spectroscopy is used. Advantages to this technique include the minimization of 1/f noise, and the removal of the sloping baseline that is present on TDL spectra (due to the fact that the laser output power increases as the laser injection current increases, and changing the laser injection current is how the laser is tuned). A combination of a slow ramp and a fast sinusoidal modulation of the wavelength can be used to drive the diode laser. Each of the first detector 130 and the second detector 132 receives this modulated intensity signal. The $N^{th}$ harmonic component is resolved by demodulating the received signal. Detection using the signal at the second harmonic (2f) can be used. The 2f lineshape is symmetric and peaks at line center due to the nature of even function. Additionally, the second harmonic (2f) provides the strongest signal of the even-numbered harmonics. By shifting detection to higher frequency, 2f spectroscopy can significantly reduce 1/f noise and thereby provide a substantial sensitivity enhancement compared to direct absorption methods. Photoacoustic spectroscopy can also be utilized.

In an optional variation, data from the first detector 130, the second detector 132 and/or other sensors associated with the system can be received by a data acquisition device. In another optional variation, these data or a subset thereof can be transmitted wirelessly to a computer or to a data acquisition device. The instrument enclosure 102 can be connected to the control unit 134 by means of a single control cable. In various implementations, the control unit 134 can be an electronics enclosure holding electronics as a free-standing control box or can be installed in a rack-mounted chassis. The control unit 134 components can be installed in a computer, within an automobile, or within another variation of electronics and electronics enclosure.

The water vapor density in the gas sample or gas stream can be determined using ratiometric measurement techniques for an absorption spectrometer where the light beam 106 has been split into two paths. The transmitted intensity T is the ratio of I to $I_0$ where $I_0$ is the intensity observed at the end of a reference beam path (in the example of FIG. 1, the second split beam 114) that does not pass through the sample cell 116 and I is the intensity observed at the end of the beam path that passes through the sample cell 116 (in the example of FIG. 1, the first split beam 112). The water vapor density, W, may be obtained from:

$$W = -\ln(T)/(kL) \quad (1)$$

where k is the absorption cross section (or absorption coefficient) and L is the optical path length within the sample chamber. Depending on the units chosen for k, W can be reported as number density (molecules per $cm^3$), vapor pressure (mbar), and the like.

As noted above, the optical beam paths internal to the instrument enclosure 102 can be configured such that the first instrument enclosure path length and the second instrument enclosure path length traveled by the first split beam 112 and the second split beam 114, respectively, are equal or approximately equal. Part of the overall beam path traveled between the light source 104 and the respective first detector 130 and second detector 132 can also be common to both legs (for example the distance between the light source 104 and the beam splitter 110). This configuration makes the optical beam paths outside of the sample chamber path length equivalent. The water vapor density inside the instrument enclosure 102 produces the same optical absorption level in the two legs, and this value cancels when the ratio $I/I_0$ is formed leaving only the absorption spectrum from the sample chamber's internal volume.

Calibration of the sensor may be accomplished according to equation 1 (which is Beer's law), for direct absorption measurements. Based on k and L, and a measurement of T, W may be computed. In one variation, no specific calibration procedure is required if the value for k is known. For measurements using a tunable laser and a modulated laser current, calibration can optionally be performed using gas streams of differing humidity, background gas composition, and/or pressure. For direct absorption measurements using a tunable laser and unmodulated laser current, the calibration can be independent of the background gas composition and pressure.

Figure 2:
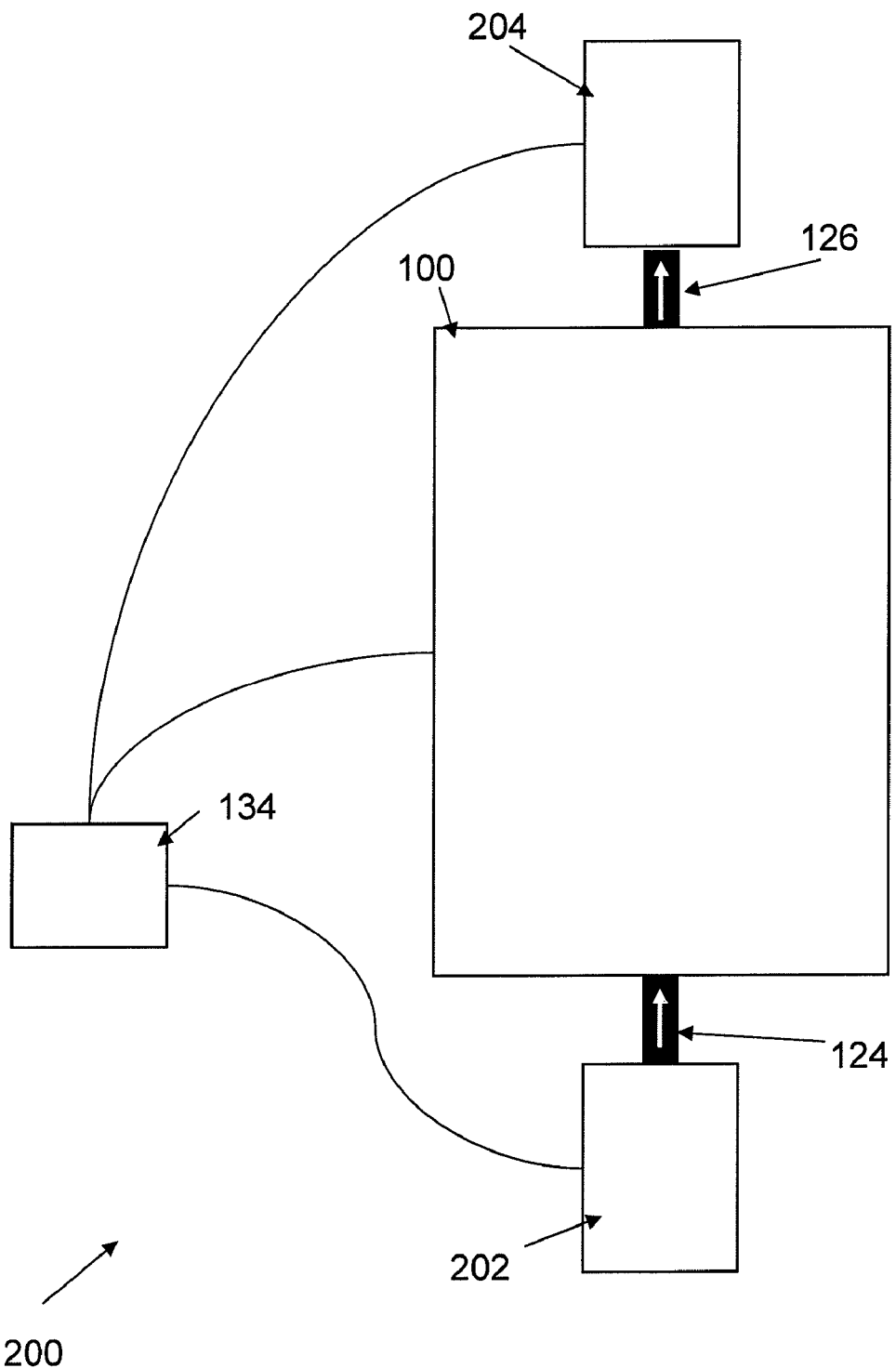
FIG. 2 is a block diagram showing a humidity sensor incorporated into a fuel cell system.

FIG. 2 shows a general view of one implementation of a fuel cell humidity sensor installed in a fuel cell system 200. In some implementations, a fuel cell system or fuel cell balance of plant can include the apparatus necessary to run, to test, and/or to maintain a polymer electrolytic membrane (PEM) fuel cell. In some implementations, the fuel cell system or fuel cell balance of plant can include components including, but not limited to, gas flow controllers, gas pressure controllers, gas temperature controllers, gas mixing mechanisms, gas humidification apparatus with water piping, tubing and tube fittings, heating mechanisms for the gas lines or for the fuel cell, power conditioners or analyzers for the fuel cell electrical output, or other controls or equipment to enable operation, testing, or maintenance of the fuel cell. In these implementations of a fuel cell system, a fuel gas stream is conditioned and possibly humidified and sent to the fuel cell by way of a gas conduit such as a tube. In these implementations of a fuel cell system, an oxidizer gas stream can optionally be conditioned and possibly humidified and sent to the fuel cell by way of a gas conduit such as a tube. In other implementations of a fuel cell system, the oxidizer can be uncontrolled and can be an air vent mechanism attached to the fuel cell. Implementations of a fuel cell system can also optionally include a system for processing or measuring the fuel gas stream and/or oxidizer gas stream after they exit the fuel cell. In some implementations of a fuel cell system, system control can be run on an embedded processor within the system, a computer within the system, a remote computer, or another method of control. An example of a fuel cell apparatus is shown as a fuel cell test station 202, a humidity sensor 100, a fuel cell 204, and a control unit 134. The fuel cell test station 202 produces a humidified flowing gas stream. The humidified flowing gas stream is supplied to the humidity sensor 100 via the inlet 124 to the sample chamber (within the instrument enclosure 102). The gas stream exits the humidity sensor 100 via the outlet 126 and enters the fuel cell under test 204. Data from the humidity sensor 100 can be received by the control unit 134 or by some other data acquisition device, a computer, or the like. The control unit 134 can also optionally be connected electronically to the fuel cell test station 202 to provide feedback on the measured humidity and/or to control the fuel cell test station 202 to change the humidity or other operating conditions. In some implementations, the sample chamber 126 can optionally be a pipe or tube or other portion of the fuel cell system, that can optionally be external to the instrument enclosure 102.

Figure 3:
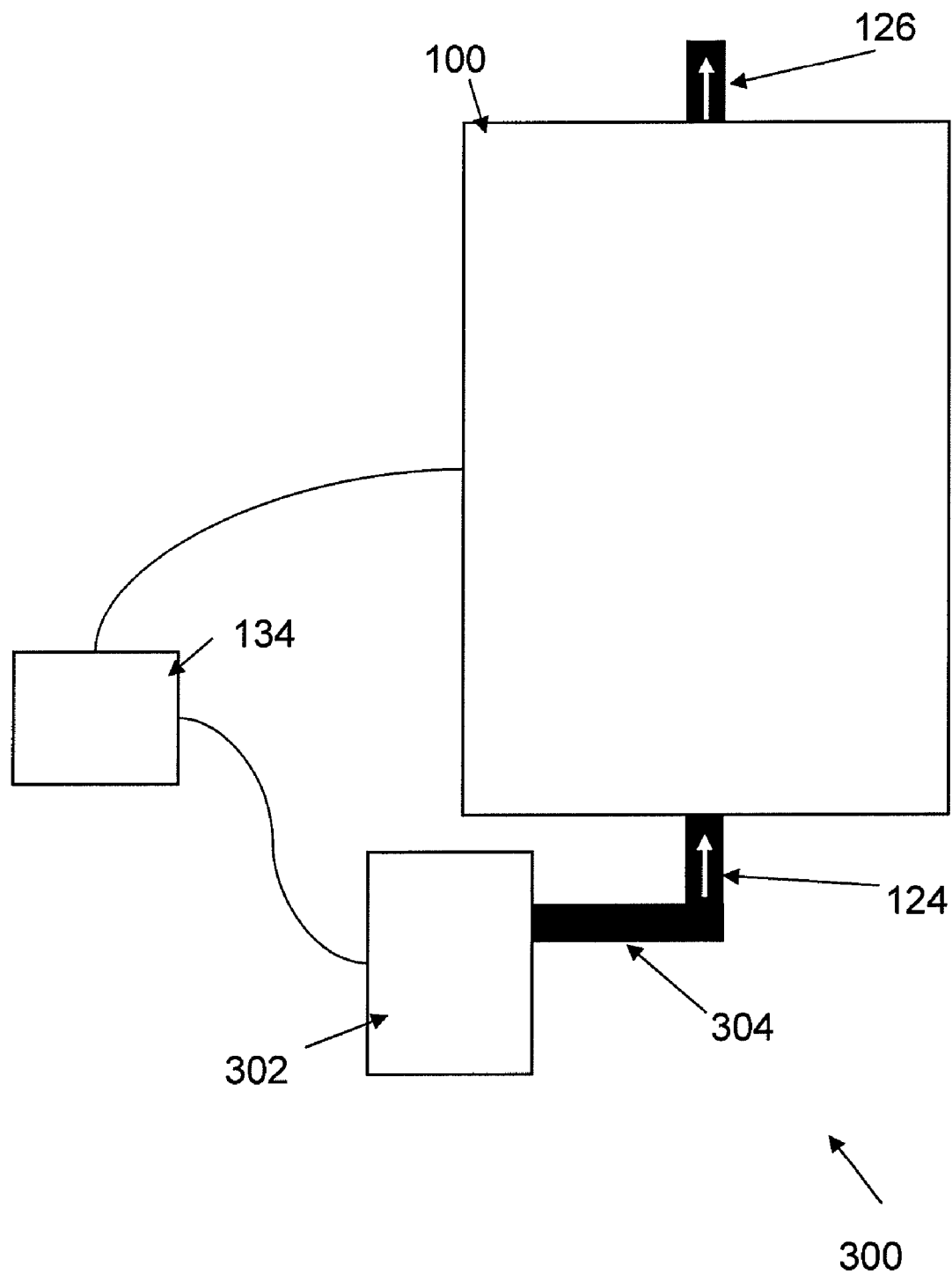
FIG. 3 is a block diagram showing a humidity sensor incorporated into a combustion device exhaust system.

In another implementation, shown in FIG. 3, a humidity sensor 100 as described above can be employed to measure the products of combustion from a combustion device, such as for example an internal combustion engine. The system 300 shown in FIG. 3 includes a humidity sensor 100 and a control unit 134. A combustion device 302 with an exhaust 304 generates an exhaust gas stream that contains products of combustion including water vapor. At least a portion of the exhaust gas stream flowing from the exhaust 304 can be directed into the inlet 124 of the humidity sensor 100. This humidified gas stream flows through the sample chamber within the humidity sensor 100. Signals from the first and second detector (130 and 132 in FIG. 1) are provided to the control unit 134 which periodically calculates the water vapor partial pressure of the humidified exhaust gas stream. The exhaust gas stream passes out of the humidity sensor outlet 126 to, for example, the ambient atmosphere, additional analytical equipment, emissions controls devices, or the like. The control unit 134 can provide signals back to the combustion device 302 to indicate the composition of the exhaust gas stream and thereby facilitate adjustment and/or optimization of the combustion process. In some implementations, the sample chamber 126 can optionally be a pipe or tube or other portion of the exhaust of a combustion device, that can optionally be external to the instrument enclosure 102.

Figure 4:
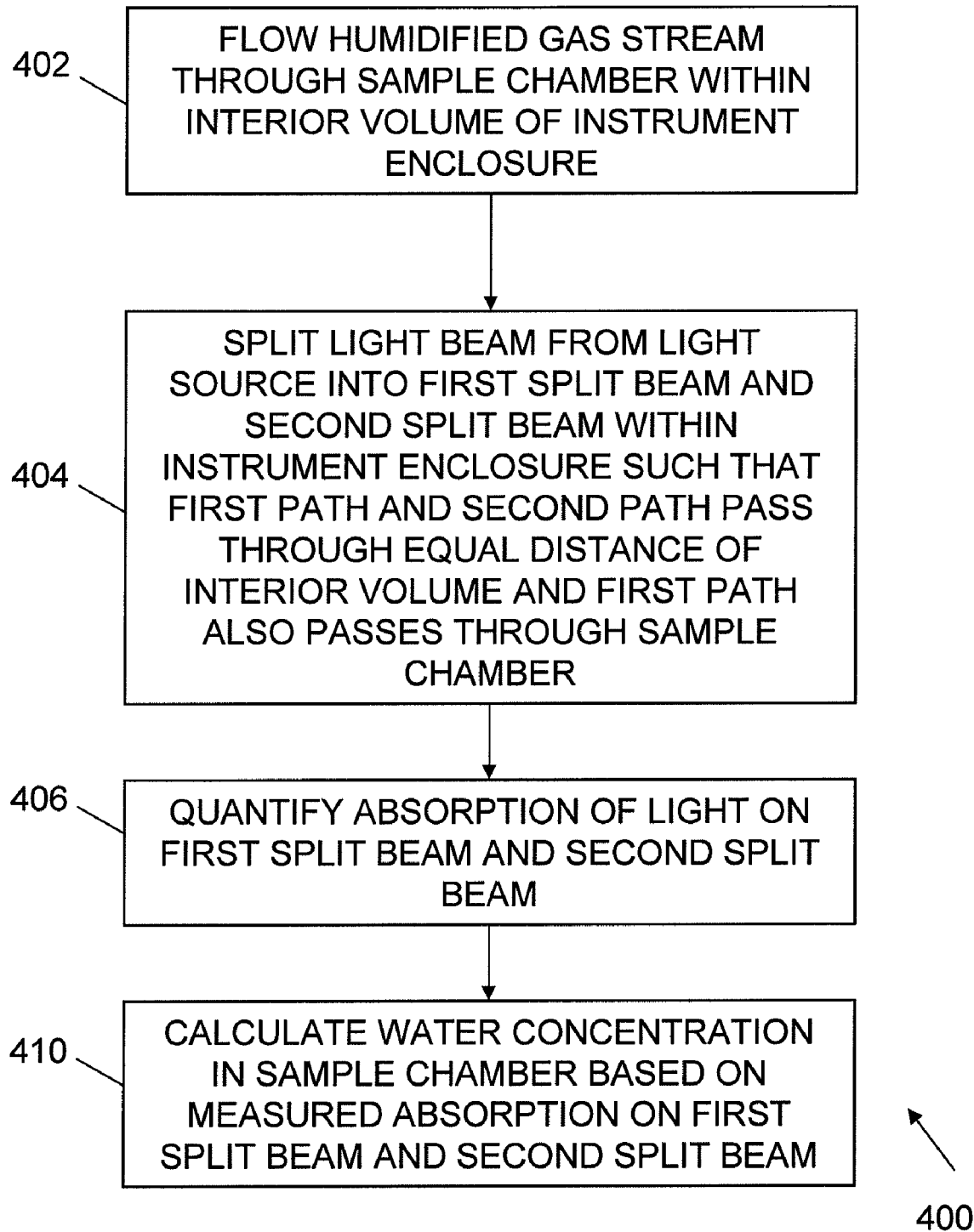
FIG. 4 is a process flow diagram illustrating a method of detecting and/or quantifying water vapor densities in gas streams.

FIG. 4 is a process flow chart 400 illustrating a method for measuring water vapor partial pressure in a flowing humidified gas stream. At 402, the flowing humidified gas stream flows through a sample chamber 116 that is contained within an interior volume of an instrument enclosure 102. The instrument enclosure 102 can, as described above, optionally be temperature controlled, optionally at approximately room temperature. The sample chamber 116 can, as described above, optionally be located outside of the instrument enclosure 102. At 404, the light beam from the light source 104 is split into a first split beam 112 and a second split beam 114. The first split beam 112 passes through the sample chamber 116 and also along a first instrument enclosure path within the instrument enclosure 102. The second split beam 114 passes only along a second instrument enclosure path length that is equal to the first instrument enclosure path length. At 406, the absorption of light for each of the first split beam 112 and the second split beam 114 are quantified such as for example as described above. The water vapor partial pressure within the sample chamber 116 is quantified at 410 based on the quantified absorptions along the first split beam 112 and the second split beam 114.

Figure 5:
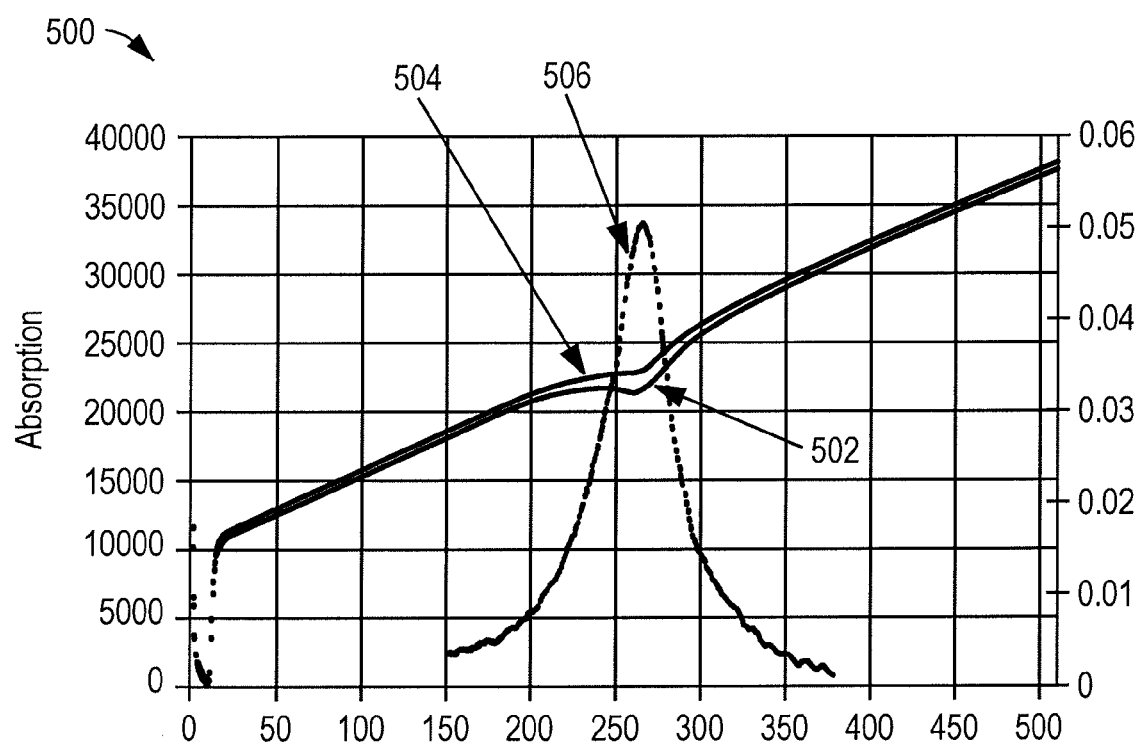
FIG. 5 is a chart showing sample absorbance spectra for a humidity sensor.

FIG. 5 shows a graph 500 of sample spectra data taken by an example of a humidity sensor as disclosed herein. As the laser scans about its wavelength range, the laser light absorption appears as a dip in the sample beam spectrum 502 and as a dip in the reference beam spectrum 504. The sample beam (first split beam 112) absorption line 502 shows greater absorption because the beam is absorbed by ambient humidity in the instrument enclosure 102 and by humidity in the gas stream under test in the sample chamber 116. The reference beam (the second split beam 114), whose absorption line 504 shows less absorption, is only subject to absorption by the ambient humidity in the instrument enclosure 102. The two spectra are normalized to each other in order to zero out any drift in the detectors or the electronics. Then the absorption curve 506 is calculated as the logarithm of the ratio of the two spectra. This removes the contribution of the ambient humidity in the enclosure and leaves only the contribution of the humidity in the sample chamber 116. According to Beer's Law, the area under the curve is proportional to the molecular density of the water vapor. Calibration of the sensor can include collecting additional data to linearize this result and to remove the effect of the gas stream temperature, since the absorption coefficient k in Beer's Law is temperature dependent.

The subject matter described herein can be embodied in systems, apparatus, methods, and/or articles depending on the desired configuration. In particular, various aspects of the subject matter described herein can be realized in digital electronic circuitry, integrated circuitry, specially designed application specific integrated circuits (ASICs), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, programmable logic devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Although a few variations have been described in detail above, other modifications, additions, and implementations are possible within the scope and spirit of the disclosed subject matter. For example, other configurations of the optical paths for the subject matter as described are within the scope of the presently disclosed subject matter. Features implementing functions can also be physically located at various positions, including being distributed such that portions of functions are implemented at different physical locations. Further features and/or variations can be provided in addition to those set forth herein. For example, the implementations described above can be directed to various combinations and subcombinations of the disclosed features and/or combinations and subcombinations of several further features disclosed above. In addition, the logic flow depicted in the accompanying figures and/or described herein do not require the particular order shown, or sequential order, to achieve desirable results.

What is claimed is:

1. An apparatus comprising:
   an instrument enclosure;
   a light source positioned within the instrument enclosure that emits a light beam;
   a beam splitter disposed to split the light beam into a first split beam and a second split beam;
   a sample chamber configured to accept a flowing humidified gas stream, the sample chamber disposed so that the first split beam passes through the sample chamber over a sample chamber path length;
   a first detector positioned within the instrument enclosure and disposed in the path of the first split beam after the first split beam passes through the sample chamber, the first detector quantifying a first intensity of light transmitted in the first split beam as the first split beam traverses a first instrument enclosure path length within the instrument enclosure and the sample chamber path length;
   a second detector positioned within the instrument enclosure and disposed in the path of the second split beam, the second detector quantifying a second intensity of light transmitted in the second split beam as the second split beam traverses a second instrument enclosure path length within the instrument enclosure, the second instrument enclosure path length being equal to the first instrument path length; and
   a controller configured to receive and interpret a first signal from the first detector and a second signal from the second detector to calculate the water vapor partial pressure or density in the flowing humidified gas stream.

2. An apparatus as in claim 1, wherein the light source is selected from a group consisting of a vertical cavity surface emitting laser, a horizontal cavity surface emitting laser, a quantum cascade laser, a distributed feedback laser, a color center laser, a light emitting diode, and an incandescent lamp.

3. An apparatus as in claim 1, wherein the light source is a tunable diode laser controlled by the controller and wherein the light beam comprises a range of wavelengths, the controller tuning the tunable diode laser across the range of wavelengths, demodulating the first signal and second signal to determine a first absorption spectrum for the first split beam and a second absorption spectrum for the second split beam, and calculating the water vapor partial pressure or density in the flowing gas stream based on the first absorption spectrum and the second absorption spectrum.

4. An apparatus as in claim 1, wherein the light source emits light with a wavelength in a range of about 1.35 to 1.39 µm or with a wavelength chosen from approximately 1.12 µm, 1.37 µm, 1.88 µm, 2.35 µm, 2.70 µm, 3.00 µm, 6.00 µm, or 6.50 µm.

5. An apparatus as in claim 1, wherein the sample chamber is positioned within the instrument enclosure.

6. An apparatus as in claim 1, wherein the sample chamber is positioned outside of the instrument enclosure.

7. An apparatus as in claim 1, wherein the sample chamber is positioned outside of the instrument enclosure and comprises a portion of the system being analyzed.

8. An apparatus as in claim 1, wherein the sample chamber is maintained at a temperature above approximately 105° C.

9. An apparatus as in claim 1, wherein the sample chamber temperature is controlled by one of an adjustable manual mechanism or an adjustable automatic mechanism.

10. An apparatus as in claim 1, wherein the instrument enclosure is maintained at a temperature in a range of approximately 20 to 35° C.

11. An apparatus as in claim 1, wherein the light source is maintained at a temperature in a range of approximately 20° to 40° C.

12. An apparatus as in claim 1, further comprising:
    an inlet to the sample chamber and an outlet from the sample chamber;
    a fuel cell system connected to the inlet, the fuel cell system providing the flowing humidified gas stream;
    a connector configured to connect a fuel cell to the outlet such that the flowing humidified gas stream from the fuel cell system is supplied to the fuel cell.

13. An apparatus as in claim 1, further comprising:
    an inlet to the sample chamber and an outlet from the sample chamber;
    a fuel cell exhaust port of a fuel cell connected to the inlet, the fuel cell providing the flowing humidified gas stream; and a connector configured to connect a fuel cell system to the outlet such that the flowing humidified gas stream from the fuel cell is supplied to the fuel cell system.

14. An apparatus as in claim 13, wherein the outlet from the sample chamber is vented to atmosphere.

15. An apparatus as in claim 1, wherein the flowing humidified gas stream is an exhaust stream emitted from a combustion device connected to an inlet on the sample chamber.

16. An apparatus as in claim 15, wherein the combustion device is an internal combustion engine.

17. An apparatus as in claim 1, further comprising an automobile with an internal combustion engine that comprises an exhaust connected to an inlet on the sample chamber, the exhaust providing the flowing humidified gas stream, the controller providing a feedback signal regarding the partial pressure or density of water vapor in the exhaust.

18. A method comprising:
splitting a beam of light from a light source into a first split beam and a second split beam;
flowing a humidified gas stream through a sample chamber;
directing the first split beam through the sample chamber and to a first detector positioned within an instrument enclosure, the first detector quantifying a first intensity of light transmitted in the first split beam as the first split beam traverses a first instrument enclosure path length within the instrument enclosure and a first sample chamber path length within the sample chamber;
directing the second split beam to a second detector positioned within the instrument enclosure, the second detector quantifying a second intensity of light transmitted in the second split beam as the second split beam traverses a second instrument enclosure path length within the instrument enclosure, the second instrument enclosure path length being equal to the first instrument path length; and
calculating and promoting a partial pressure or density of water vapor in the sample chamber based on the first intensity of light and the second intensity of light.

19. A method as in claim 18, wherein the promoting comprises one or more of displaying, transmitting, or storing the partial pressure or density of water vapor in the sample chamber.

20. A method as in claim 18, further comprising periodically determining the partial pressure or density of water vapor in the humidified gas stream.

21. A method as in claim 18, wherein the light source is selected from a group consisting of a vertical cavity surface emitting laser, a horizontal cavity surface emitting laser, a quantum cascade laser, a distributed feedback laser, a color center laser, a light emitting diode, and an incandescent lamp.

22. A method as in claim 18, wherein the light source is a tunable diode laser and wherein the light beam comprises a range of wavelengths; further comprising:
tuning the tunable diode laser across the range of wavelengths; and
demodulating a first signal received from the first detector and a second signal received from the second detector to determine a first absorption spectrum for the first split beam and a second absorption spectrum for the second split beam; and
calculating the water vapor partial pressure or density in the sample chamber based on the first absorption spectrum and the second absorption spectrum.

23. A method as in claim 18, wherein the quantifying of the absorption at the selected wavelength is accomplished using one of direct absorption spectroscopy, harmonic spectroscopy, photoacoustic spectroscopy, integrated cavity spectroscopy, and cavity enhanced spectroscopy.

24. A method as in claim 18, wherein the light beam comprises light at a wavelength in a range of approximately 1.35 to 1.39 μm or at a wavelength chosen from approximately 1.12 μm, 1.37 μm, 1.88 μm, 2.35 μm, 2.70 μm, 3.00 μm, 6.00 μm, or 6.50 μm.

25. A method as in claim 18, wherein the sample chamber is positioned inside the instrument enclosure.

26. A method as in claim 18, wherein the sample chamber is positioned outside of the instrument enclosure.

27. A method as in claim 18, wherein the sample chamber is positioned outside of the instrument enclosure and comprises of a portion of a system being analyzed.

28. A method as in claim 18, further comprising maintaining the sample chamber at a temperature above approximately 105° C.

29. A method as in claim 18, wherein the sample chamber temperature is controlled by one of an adjustable manual mechanism or an adjustable automatic mechanism.

30. A method as in claim 18, further comprising maintaining the instrument enclosure at a temperature in a range of approximately 20 to 35° C.

31. A method as in claim 18, further comprising maintaining the light source at a temperature in a range of approximately 20° to 40° C.

32. A method as in claim 18, further comprising:
flowing the humidified gas stream from a fuel cell system to a fuel cell being operated via the sample chamber and, flowing the humidified gas stream from a fuel cell to a fuel cell system via the sample chamber, or flowing the humidified gas stream from a fuel cell to atmosphere via the sample chamber; and
calculating the water vapor partial pressure or density in the humidified gas stream at a periodic interval.

33. A method as in claim 32, wherein the periodic interval is approximately 1 second.

34. A method as in claim 32, wherein the calculating is performed by a controller and further comprising providing a feedback signal from the controller to the fuel cell system based on the measured water vapor density to maintain the water vapor partial pressure or density in the gas stream at a constant level.

35. A method as in claim 18, wherein the humidified gas stream is an exhaust stream from a combustion device and wherein the promoting comprises providing a feedback signal to the combustion device regarding the partial pressure or density of water vapor in the exhaust stream.

* * * * *